(12) United States Patent
Watari et al.

(10) Patent No.: US 6,737,021 B2
(45) Date of Patent: May 18, 2004

(54) AUTOMATIC ANALYZER

(75) Inventors: Shigenori Watari, Hitachinaka (JP);
Hajime Katou, Chiyoda-machi (JP);
Katsuhiro Kambara, Hitachinaka (JP);
Hiroyasu Uchida, Hitachinaka (JP);
Takeshi Shibuya, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 507 days.

(21) Appl. No.: 09/789,625

(22) Filed: Feb. 22, 2001

(65) Prior Publication Data
US 2001/0019702 A1 Sep. 6, 2001

(30) Foreign Application Priority Data

Feb. 25, 2000 (JP) .......................... 2000-50034
Feb. 29, 2000 (JP) .......................... 2000-54955

(51) Int. Cl.[7] ........................... B32B 5/00; G01N 21/00; G01N 31/00; G01N 33/00; G01N 15/06; B01F 11/02
(52) U.S. Cl. ..................... 422/63; 422/68.1; 366/127
(58) Field of Search ................... 422/63, 68.1; 366/127

(56) References Cited

U.S. PATENT DOCUMENTS

| 5,236,664 | A | * | 8/1993 | Ludvigsen | 422/44 |
| 5,286,451 | A | * | 2/1994 | De Silva et al. | 422/68.1 |
| 5,484,573 | A | | 1/1996 | Berger et al. | |
| 5,529,753 | A | * | 6/1996 | Haddad et al. | 422/64 |
| 5,736,100 | A | * | 4/1998 | Miyake et al. | 422/64 |
| 5,846,491 | A | * | 12/1998 | Choperena et al. | 422/67 |
| 5,874,046 | A | * | 2/1999 | Megerle | 422/68.1 |
| 2003/0203491 | A1 | * | 10/2003 | Andrevski et al. | 436/46 |

FOREIGN PATENT DOCUMENTS

| JP | 57-028182 | | 2/1982 |
| JP | 5-317820 | | 12/1993 |
| JP | 7-311204 | | 11/1995 |
| JP | 408146007 A | * | 6/1996 |
| JP | 2000-146986 | | 5/2000 |

* cited by examiner

*Primary Examiner*—Jill Warden
*Assistant Examiner*—Brian R. Gordon
(74) *Attorney, Agent, or Firm*—Mattingly, Stanger & Malur, P.C.

(57) ABSTRACT

Multiple piezoelectric elements 35 are arranged in a row along the top of liquid level in a reaction vessel 11. An ultrasonic reflecting material 38 is installed on the bottom of the portion of the heat insulating bath 12 where heat insulating medium 13 is stored. A lateral ultrasonic wave 9b is generated on the lower side by actuation of the piezoelectric element 35. Wave 9b is reflected by the ultrasonic reflecting material 38. As lower ultrasonic wave 8 advances along the wall surface of the reaction vessel, it collides with the specimen liquid, thereby causing a portion of the liquid level closer to the piezoelectric element 35 to be raised. When lateral ultrasonic wave 9a is applied to this portion, it reaches the inclined portion of the raised liquid level of the specimen. Swirling flow by agitation 36 is produced by acoustic radiation pressure of the ultrasonic wave. The specimen and reagent are mixed and agitated by this swirling flow.

6 Claims, 9 Drawing Sheets

FIG. 13(a)

| ANALYSIS ITEM | IRRADIATION POSITION |
|---|---|
| ANALYSIS ITEM A | IRRADIATION POSITION A |
| ANALYSIS ITEM B | IRRADIATION POSITION B |
| ⋮ | ⋮ |

FIG. 13(b)

| ANALYSIS ITEM | SAMPLE QUANTITY | REAGENT QUANTITY |
|---|---|---|
| ANALYSIS ITEM A | QUANTITY AA | QUANTITY aa |
| ANALYSIS ITEM B | QUANTITY BB | QUANTITY bb |
| ⋮ | ⋮ | ⋮ |

FIG. 13(c)

| ANALYSIS ITEM | IRRADIATION INTENSITY |
|---|---|
| ANALYSIS ITEM A | IRRADIATION INTENSITY A |
| ANALYSIS ITEM B | IRRADIATION INTENSITY B |
| ⋮ | ⋮ |

FIG. 13(d)

| REAGENT DATA | IRRADIATION INTENSITY |
|---|---|
| REAGENT DATA A | IRRADIATION INTENSITY A |
| REAGENT DATA B | IRRADIATION INTENSITY B |
| ⋮ | ⋮ |

# AUTOMATIC ANALYZER

BACKGROUND OF THE INVENTION

The resent invention relates to the automatic analyzer which uses reagent or the like to analyze the components of the specimen as objects of analysis, and particularly to the automatic analyzer provided with an agitator to ensure that reagent required for analysis of specimen components is mixed with the specimen.

To mix reagent with the specimen in the agitator of the conventional automatic analyzer, an agitating rod 61 having a spatula-shaped tip is inserted into the reaction vessel where reagent is mixed with the specimen, and the agitating rod is rotated or moved in reciprocating motion.

For example, the agitating rod 61 having a spatula-shaped tip is inserted into the reaction vessel 11 containing a mixture of reagent and specimen as shown in FIG. 9(*a*), and the agitating rod 61 is rotated by an actuator 60. Or the agitating rod 61 having a spatula-shaped tip is inserted into the reaction vessel 11 containing a mixture of reagent and specimen as shown in FIG. 9(*b*), and the agitating rod 61 is moved in reciprocating motion by an actuator 60.

When this conventional automatic analyzer is used, a trace amount of chemicals or specimens deposited on the agitating rod will cause a phenomenon called carry-over which affects the result of the next analysis. This requires some means to clean the agitating rod.

Official Gazette of Japanese Patent Laid-Open NO.311204/1997 discloses an example of using a piezoelectric element as dispensing nozzle cleaning means. The cleaning means disclosed in this Journal gives mechanical oscillation to the nozzle itself to remove reagent or specimen deposited on the dispensing nozzle. It uses oscillation of the piezoelectric element to improve nozzle cleaning effect. This is not effective as an agitating means to promote mixing between reagent and specimen.

To reduce physical loads of the specimen provider or to cut down system running costs for the automatic analyzer, efforts are made to reduce the amount of the specimen and reagent required for analysis of each item.

In this case, if the amount of the specimen and reagent is reduced in the reaction vessel having the same capacity as that of the conventional reaction vessel as shown in FIG. 10(*b*), the area which light to be measured passes by will be smaller than when the amount of the specimen and reagent shown in FIG. 10(*a*) is not reduce. This will result in reduced measuring accuracy.

To get an accurate measurement of the reduced amount of the specimen and reagent, it is necessary to reduce the capacity of the reaction vessel and to secure the liquid level of the specimen and reagent and light transmission area, as shown in FIG. 10(*c*).

However, it becomes difficult to physically insert and to reciprocate the agitating rod due to reduced capacity of the reaction vessel in case of the automatic analyzer using the reaction vessel having a reduced capacity, where the agitating rod having a spatula-shaped tip in the agitator to mix the reagent with the specimen is inserted into said reaction vessel to rotate the agitating rod or move it in reciprocating motion. Therefore, an agitation mechanism to agitate the reagent with the specimen without using the agitating rod becomes to be needed.

Furthermore, even if the agitating rod is cleaned, it is impossible to completely eliminate the phenomenon of carry-over where a trace amount of specimen or reagent is carried over to the next analysis. It is also impossible to eliminate the possibility of water for cleaning being brought into the reaction vessel by the agitating rod.

Said carry-over and transfer of cleaning water into the vessel will have some adverse effect on the result of analysis when the capacity of the reaction vessel is reduced and the quality of reagent and specimen is decreased.

SUMMARY OF THE INVENTION

The object of the present invention is to provide an automatic analyzer which is capable of effective agitation of the reagent and specimen, in a case to be difficult to insert the agitation rod because of a small capacity of the reaction vessel, by a method to agitate the reagent and specimen without touching thereto and without carry-over between specimens or water brought into the next process, thereby ensuring highly reliable results of analysis.

The above object can be attained by the present invention which is configured as described below:

(1) An automatic analyzer comprises the following:

an analyzer unit to analyze the components of a specimen to be analyzed, a heat insulating bath to support a reaction vessel and to hold the heat insulating medium to keep a constant temperature of liquid mixture between said specimen for analysis stored in said reaction vessel and reagent or others, a controller to administer and control the entire system including said analyzer unit, an agitator installed on the side of the reaction vessel supported by said heat insulating bath, wherein said agitator comprises multiple ultrasonic generators to generate lateral ultrasonic wave and a reflecting means to reflect ultrasonic wave from said ultrasonic generators and to irradiate lower ultrasonic wave toward the liquid level of liquid mixture from the bottom of said reaction vessel, and said agitator mixes and agitates the specimen in the reaction vessel, reagent or the like using the swirling flow generated by acoustic radiation pressure by coordination between said lateral ultrasonic wave and lower ultrasonic wave, and an ultrasonic generator drive circuit to supply drive power to said ultrasonic generator.

(2) An automatic analyzer comprises the following:

an analyzer unit to analyze the components of a specimen to be analyzed, a heat insulating bath to support a reaction vessel and to hold the heat insulating medium to keep a constant temperature of liquid mixture between said specimen for analysis stored in said reaction vessel and reagent or others, wherein the bottom is inclined with respect to said liquid mixture level to serve as an ultrasonic wave reflecting means, a controller to administer and control the entire system including said analyzer unit, an agitator installed on the side of the reaction vessel supported by said heat insulating bath, wherein said agitator comprises multiple ultrasonic generators to generate lateral ultrasonic wave, and said agitator mixes and agitates the specimen in the reaction vessel, reagent or the like using the swirling flow generated by acoustic radiation pressure by coordination between lower ultrasonic wave and said lateral ultrasonic wave;

wherein said lower ultrasonic wave is generated when ultrasonic wave generated from said ultrasonic generator is reflected against the bottom of said heat insulating bath, and said lower ultrasonic wave is irradiated from the bottom of said reaction vessel toward the liquid mixture level, and an ultrasonic generator drive circuit to supply drive power to said ultrasonic generator.

(3) An automatic analyzer comprises the following:

an analyzer unit to analyze the components of a specimen to be analyzed, a reaction vessel storing the specimen for analysis and liquid mixture with reagent or the like, wherein the bottom is inclined with respect to said liquid mixture level to serve as an ultrasonic wave reflecting means, a heat insulating bath to support a reaction vessel and to hold the heat insulating medium to keep a constant temperature of liquid mixture between said specimen for analysis stored in said reaction vessel and reagent or others, a controller to administer and control the entire system including said analyzer unit, an agitator installed on the side of the reaction vessel supported by said heat insulating bath, wherein said agitator comprises multiple ultrasonic generators to generate lateral ultrasonic wave, and said agitator mixes and agitates the specimen in the reaction vessel, reagent or the like using the swirling flow generated by acoustic radiation pressure by coordination between lower ultrasonic wave and said lateral ultrasonic wave;

wherein said lower ultrasonic wave is generated when ultrasonic wave generated from said ultrasonic generator is reflected against the bottom of said reaction vessel, and said lower ultrasonic wave is irradiated toward the liquid level of said liquid mixture stored in said reaction vessel, and an ultrasonic generator drive circuit to supply drive power to said ultrasonic generator.

(4) An automatic analyzer described in above (1), (2) and (3) preferably characterized in that the material of said ultrasonic wave reflecting means has acoustic impedance different from that of the heat insulating medium in the heat insulating bath which transmits ultrasonic wave generated from the ultrasonic generator.

(5) An automatic analyzer in above (1) and (2) characterized in that said ultrasonic wave reflecting means has a mechanism to change the ultrasonic irradiation position and ultrasonic irradiation angle.

The ultrasonic generator is actuated, and the lower ultrasonic wave reflected by the ultrasonic wave reflecting means advances along the wall surface of the reaction vessel to collide with a liquid level part of liquid mixture which is closer to a lateral ultrasonic generator, thereby the liquid level part being closer to the lateral ultrasonic generator than a center of the reaction vessel is raised higher than the liquid level part not being closer to the lateral ultrasonic generator than the center of the reaction vessel. Lateral ultrasonic wave is applied to this raised portion.

BRIEF DESCRIPTION OF THE DRAWINGS

FIG. 13 is an illustration representing the configuration of various tables related to the embodiment according to the present invention.

DETAILED DESCRIPTION OF THE PREFERRED EMBODIMENTS

The following describes the details of the embodiments of the present invention with reference to the drawings.

(First Embodiment)

Figure 1:
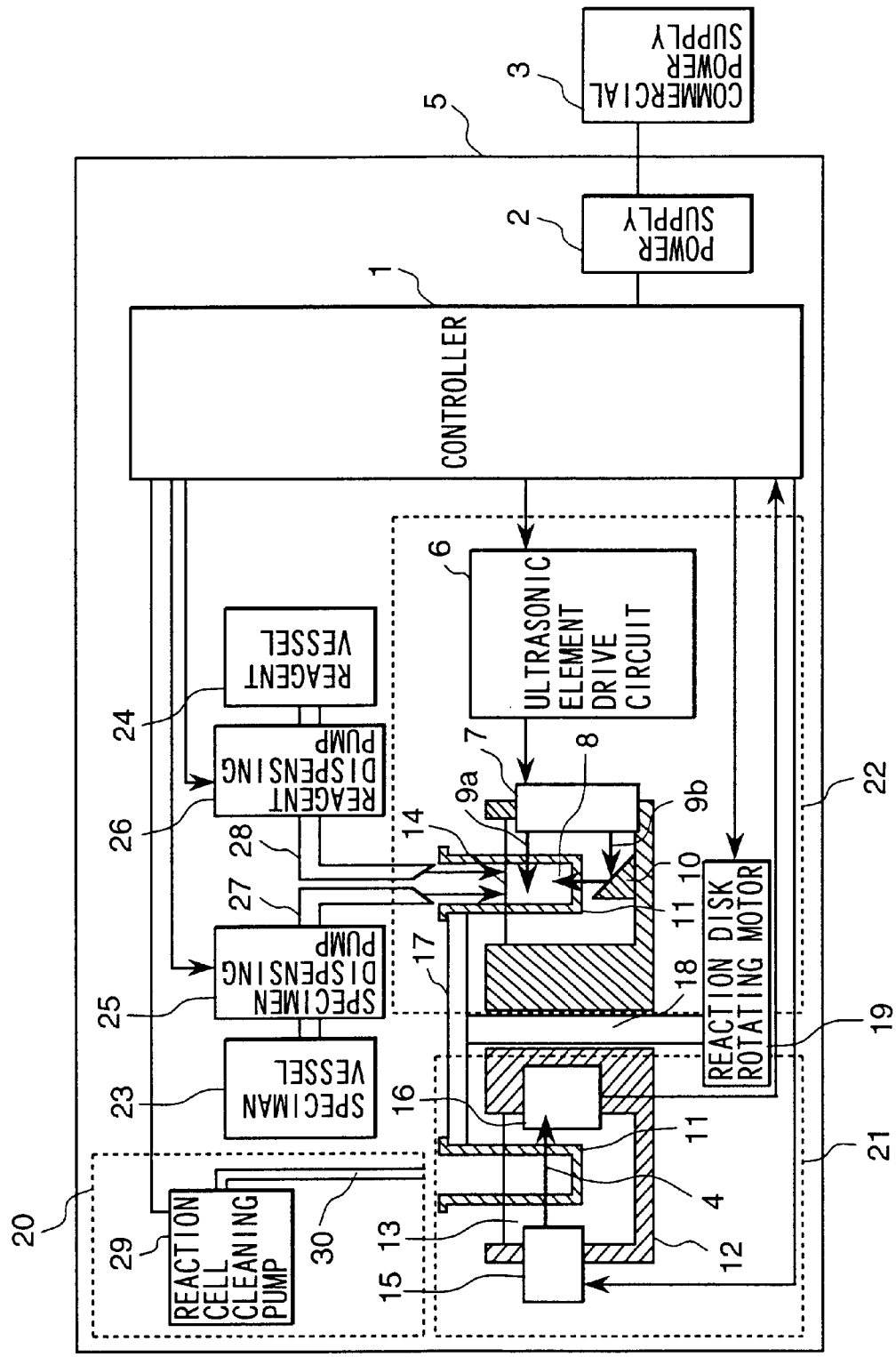
FIG. 1 is a schematic block diagram representing the first embodiment of the automatic analyzer according to the present invention.
Figure 2:
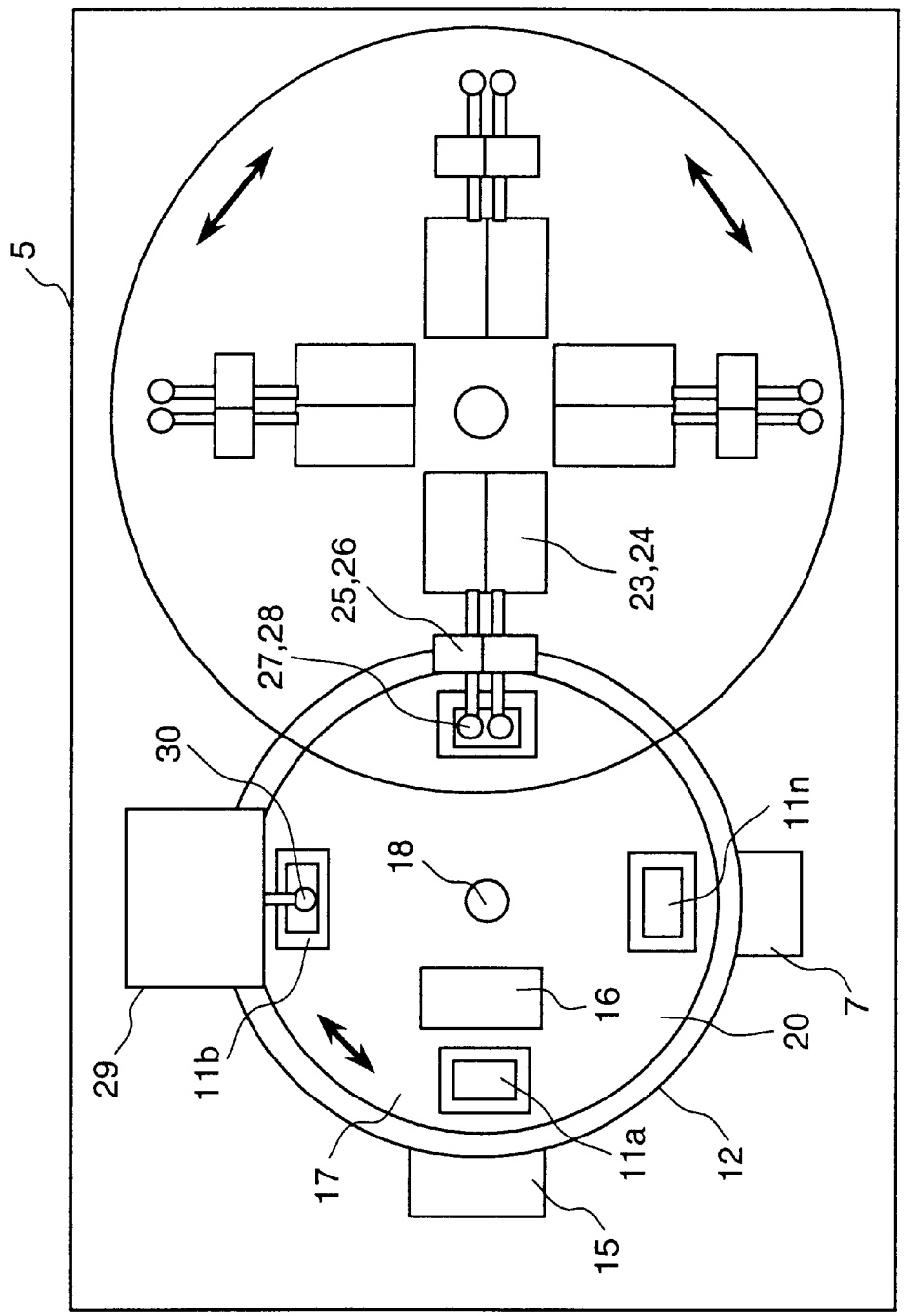
FIG. 2 is a partial plan representing the analyzer of FIG. 1.
Figure 3:
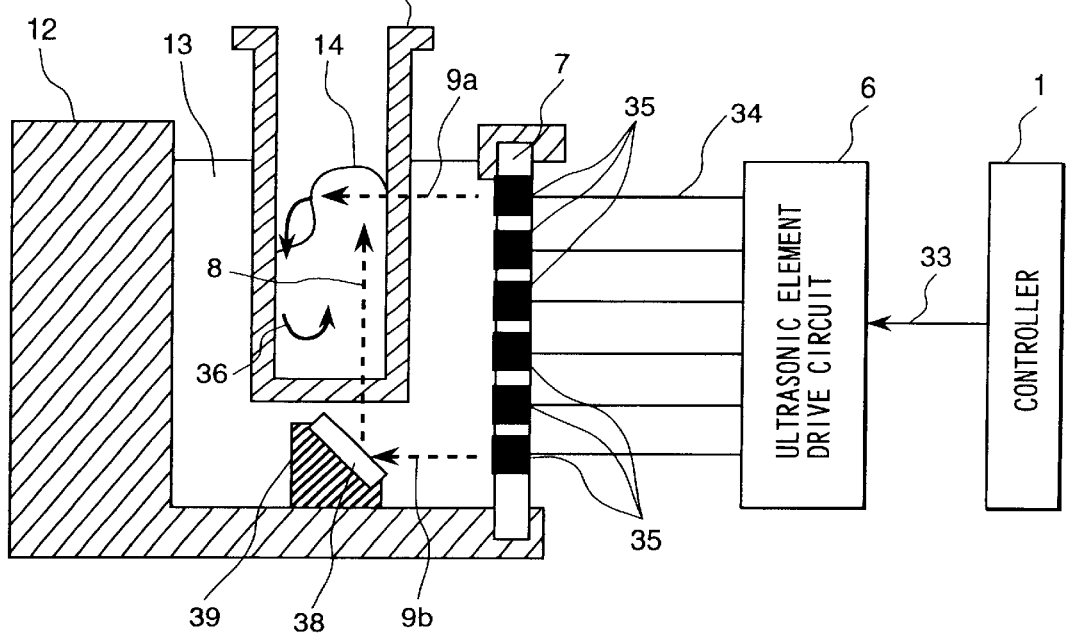
FIG. 3 is a schematic cross sectional view representing of the major portion related to the first embodiment according to the present invention.

Using FIGS. 1 to 4, the following describes the first embodiment of the automatic analyzer according to the present invention:

FIG. 1 is a schematic cross sectional view representing a part of the automatic analyzer according to the present invention. FIG. 2 is a partial plan representing the analyzer of FIG. 1. FIG. 3 is a schematic cross sectional view representing of the major portion related to the first embodiment according to the present invention.

Controller 1 in FIGS. 1 and 2 comprises an information processing system or sequencer provided with a CPU, memory and I/O. Using the automatic analysis and diagnosis program and data stored in the memory, said controller processes or administers and controls the operation of the automatic analyzer 5 and information required for analysis operation through the CPU.

Detector 21 comprises a reaction vessel 11 to mix between reagent and specimen, a light emitting unit 15 to generate light 4 to be applied to said reaction vessel 11, and a light receiving unit 16 to detect the changes in the state of the specimen and reagent in the reaction vessel 11 in terms of absorbance. The illumination level detected by the light receiving unit 16 is sent as data to the controller 1 where it is processed.

The agitator 22 mixes and agitates the specimen sent to the reaction vessel 11 from the specimen vessel 23 by the specimen dispensing pump 25 through the specimen dispensing probe 27, and the reagent sent to the reaction vessel 11 from the reagent vessel 24 by the reagent dispensing pump 26 through the reagent dispensing probe 28. In this process, said agitator uses swirling flow by agitation 36 (shown in FIG. 3) caused by ultrasonic waves generated from the ultrasonic generator 7.

Reaction vessels 11 located at the agitator 22 and detector 21 are immersed in the heat insulating medium 13 represented by water in the circular heat insulating bath 12, and are kept at a constant temperature.

Cleaner 20 consists of a reaction vessel cleaning nozzle 30 to discharge water to clear the reaction vessel 11 and to suck the water used for cleaning and waste water, and a reaction vessel cleaning pump 29.

The multiple reaction vessel 11 is mounted on the reaction disk 1, and the reaction disk rotating shaft 18 is connected to the reaction disk motor 19. The reaction disk motor 19 is controlled by the controller 1, thereby causing rotating or movement together with the reaction disk 17, and traveling through agitator 22, detector 21 and cleaner 20.

The ultrasonic element drive circuit 6 is a circuit used for the piezoelectric element 35 (given in FIG. 3) to generate the frequency and voltage produced by ultrasonic wave and to apply the voltage to the piezoelectric element 35. It is controlled by the controller 1, and serves to oscillate the piezoelectric element 35 and to generate ultrasonic waves.

Figure 4:
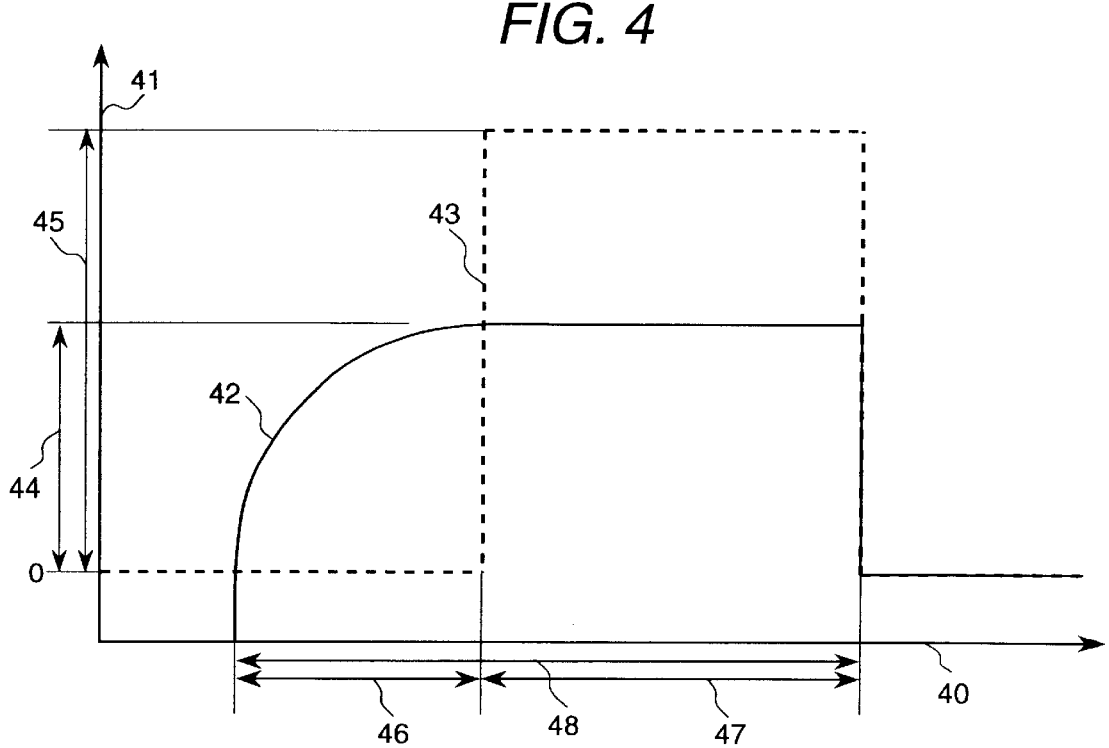
FIG. 4 is time chart showing the operation of the ultrasonic agitator.

The following describes the structure and operation of the agitator 22 in details:

When the specimen as a mixture of the specimen and reagent are to be mixed and agitated sufficiently as required for analysis in the reaction vessel 11 located in the agitator 22, the lower acoustic wave 8 and lateral ultrasonic wave 9a shown in FIG. 3 are controlled according to the sequence shown in FIG. 4, thereby producing swirling flow by agitation 36.

Piezoelectric element for lateral irradiation 35 at the position where lateral ultrasonic wave 9a and lateral ultrasonic wave 9b on the lower side are produced is laid out to ensure that irradiation position can be changed in conformance to the amount of specimen in reaction vessel 11.

Namely, multiple piezoelectric elements 35 (ultrasonic generators) are arranged in a row along the height of liquid level in the reaction vessel 11, or the electrode of one piezoelectric element is split into multiple segments, which are formed in an array along the height of liquid level in the reaction vessel 11.

The piezoelectric element for lateral irradiation 35 at the position where the lateral ultrasonic wave 9b on the lower side is generated is actuated, and the piezoelectric element for lateral irradiation 35 at the liquid level position is actuated in conformance to a particular situation, namely, in conformance to liquid level in the reaction vessel 11.

An ultrasonic reflecting material 38 is installed through support/positioning mechanism 39 on the bottom of the portion of the heat insulating bath 12 where heat insulating medium 13 is stored.

According to the operation sequence of the piezoelectric element for lateral irradiation 35, lateral ultrasonic wave 9b on the lower side is generated by actuation of the piezoelectric element for lateral irradiation 35 located at the bottom in FIGS. 3 and 4 (piezoelectric element for lateral irradiation 35 at the position where lateral ultrasonic wave 9b on the lower side is generated).

As shown in FIG. 4, said lateral ultrasonic wave 9b is gradually increased from 0 level to the level of maximum ultrasonic strength applied to lower position 44 during the voltage application period for lower element transition 46.

Lateral ultrasonic wave 9b is reflected by the ultrasonic reflecting material 38 on the forward position, and its direction is changed to upward direction. Having been changed into lower ultrasonic wave 8, it enters the bottom of reaction vessel 11, and advances in the specimen along the wall surface close to the ultrasonic element 35 of the reaction vessel 11 to collide with the liquid level in the specimen. Then part of the specimen liquid level being closer to the ultrasonic element 35 of the reaction vessel 11 than a center of the reaction vessel is raised to be higher than the part of the specimen liquid level not being closer to the ultrasonic element 35 by acoustic radiation pressure of ultrasonic wave.

Then lateral ultrasonic wave 9a is applied to the raised potion of the specimen being closer to the ultrasonic element 35 in the reaction vessel 11 by acoustic radiation pressure. Namely, after the lateral ultrasonic wave 9b has the maximum application intensity 44, lateral ultrasonic wave 9a is applied to the raised portion of the specimen at the ultrasonic strength applied to lateral position 43 on the specimen liquid level, as shown in broken line 43 of FIG. 4.

Then lateral ultrasonic wave 9a reaches the inclined part of the raised portion of the specimen through coordination with the lateral ultrasonic wave 9a and lateral ultrasonic wave 9b. Swirling flow by agitation 36, with specimen liquid level as a starting point, is produced by the acoustic radiation pressure of the ultrasonic wave. The specimen and reagent are mixed and agitated by said swirling flow by agitation 36.

According to the first embodiment of the present invention, multiple ultrasonic elements are arranged along the direction of the liquid level on the side of the reaction vessel 11 containing the specimen. Ultrasonic wave generated from the ultrasonic generating elements located on the lower side is reflected by ultrasonic reflecting mechanism 10, thereby raising the specimen liquid level. After that, ultrasonic wave is irradiated to said raised portion from the side of the reaction vessel 11 to agitate the specimen.

Thus, this method according to the present invention provides an automatic analyzer capable of ensuring an effective agitation of the reagent and specimen, hence, highly reliable results of analysis, despite the simple configuration and small size of the reaction vessel, without carry-over among specimens or water brought into the next process of analysis.

The ultrasonic reflecting material 38 of the ultrasonic reflecting mechanism 10 which changes the direction by reflecting the lateral ultrasonic wave 9b uses the substance having the acoustic impedance different from that of the heat insulating medium 13 which ensures that the ultrasonic wave generated from the piezoelectric element is transmitted to the reaction vessel 11. Generally, it is effective in using such substances as glass and SUS having the acoustic impedance greater than that of the heat insulating medium 13 which transmits the ultrasonic wave.

In the first Embodiment according to the present invention, agitators 22 are installed at one position. They can also be installed in multiple positions according to the reaction speed of the reagent.

(Second Embodiment)

Figure 5:
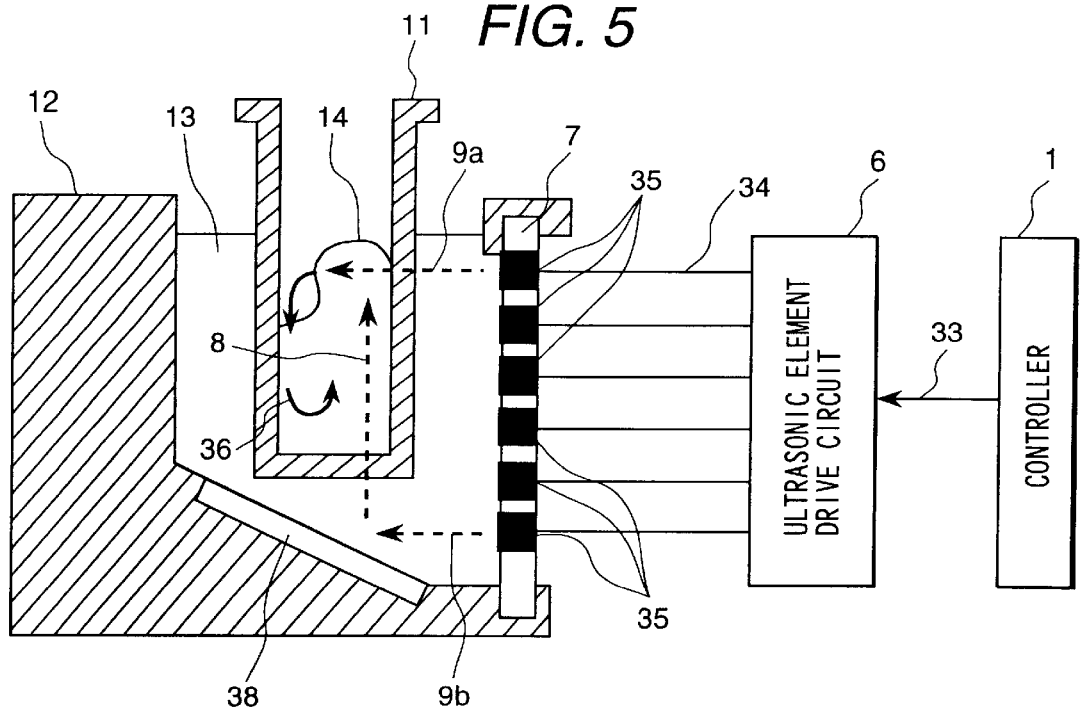
FIG. 5 is a schematic cross sectional view representing the major portion of the second embodiment according to the present invention.

FIG. 5 is a schematic cross sectional view representing the major portion of the second Embodiment of the automatic analyzer according to the present invention. The portions other than the configuration shown in FIG. 5 are the same as those shown in the first Embodiment, so they will not be illustrated or described.

In this second Embodiment given in FIG. 5, the bottom of the position corresponding to the agitator 22 is designed in an inclined structure, wherein said bottom is placed face to face with the bottom 8 of the reaction vessel 11 of the heat insulating bath 12. The ultrasonic reflecting mechanism 10 is designed to ensure that the lateral ultrasonic wave 9b generated by the piezoelectric element 35 is reflected to proceed along the side wall (side wall close to piezoelectric element 35) of this reaction vessel 11 from the bottom of the reaction vessel 8. This allows the lateral ultrasonic wave 9b to proceed in the upward direction so that it can be used as the lower ultrasonic wave 8.

The ultrasonic wave generation actuation sequence is configured to actuate the piezoelectric element for lateral irradiation 35 located at the bottom and to generate the lateral ultrasonic wave 9b. Lateral ultrasonic wave 9b is reflected by the ultrasonic reflecting material 38 on the forward position so that it proceeds upward. As a lower ultrasonic wave 8, it enters the bottom of the reaction vessel 11. The lower ultrasonic wave 8 proceeds in the specimen to collide with the specimen liquid level, and the specimen liquid level is raised by the acoustic radiation pressure of ultrasonic wave.

Then lateral ultrasonic wave 9a reaches the inclined portion of the liquid level raised by application of lateral ultrasonic wave 9a to the raised portion of the specimen in the reaction vessel. Swirling flow by agitation 36 with the specimen liquid level as a starting point is produced by the acoustic radiation pressure of ultrasonic wave. The specimen and reagent are mixed and agitated by the swirling flow by agitation 36.

As described above, according to the second Embodiment of the present invention, the same effect as that of the first Embodiment can be obtained.

According to the second Embodiment of the present invention, if the bottom is designed in an inclined structure over the entire circumference of the heat insulating bath 12, the flow channel area of the heat insulating medium 13 circulating in the heat insulating bath 12 can be made almost the same over the entire circumference of the heat insulating bath 12. This ensures that the flow velocity of the heat insulating medium 13 is constant to minimize the changes in the temperature of the specimen in the reaction vessel 11. This makes it possible to get more stable measurement data.

(Third Embodiment)

Figure 6:
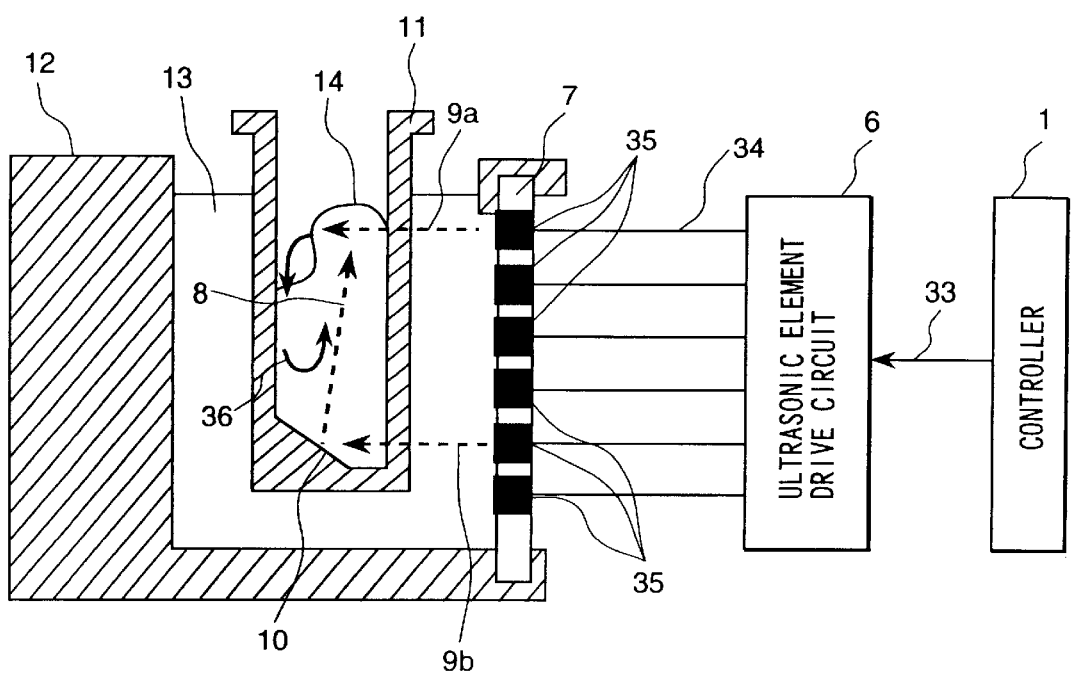
FIG. 6 is a schematic cross sectional view representing the major portion of the third embodiment according to the present invention.

FIG. 6 is a schematic cross sectional view representing the major part of the automatic analyzer according to the third Embodiment of the present invention. The portions other than the configuration shown in FIG. 6 are the same as those shown in the first Embodiment, so they will not be illustrated or described.

The bottom inside the reaction vessel 11 of the automatic analyzer in FIG. 6 is designed in an inclined structure to create the mechanism which ensures that lateral ultrasonic wave 9b generated by the piezoelectric element 35 is reflected to proceed to the liquid level from the bottom of the reaction vessel 11. This allows the lateral ultrasonic wave 9b to proceed upward; thus, it can be used as lower ultrasonic wave 8.

The sequence to actuate ultrasonic wave generation actuates the piezoelectric element for lateral irradiation 35 located at the bottom to generate lateral ultrasonic wave 9b. Lateral ultrasonic wave 9b enters the reaction vessel 11 from the side, and is reflected by the inclined structure of the bottom of the reaction vessel 11. Then it proceeds upward to advance through the specimen as lower ultrasonic wave 8. Then lower ultrasonic wave 8 collides with the specimen liquid level, and part of the specimen liquid level is raised by the acoustic radiation pressure of ultrasonic wave.

Then lateral ultrasonic wave 9a is applied to the raised portion of the specimen in the reaction vessel 11. Lateral ultrasonic wave 9a reaches the inclined portion of the raised liquid level, and swirling flow by agitation 36 with the specimen liquid level as a starting is produced by the acoustic radiation pressure of ultrasonic wave. The specimen and reagent are mixed and agitated by said swirling flow by agitation 36.

The same effect as that of the first Embodiment cab be obtained according to the third Embodiment of the present invention.

In contrast to the first and second Embodiments, the third Embodiment of the present invention does not require installation of any structure in the heat insulating bath 12. This provides the effect of simplifying the structure of the heat insulating bath 12 and reducing the manufacturing cost.

The material of the reaction vessel 11 may be plastic, but is preferred to be glass.

(Fourth Embodiment)

Figure 7:
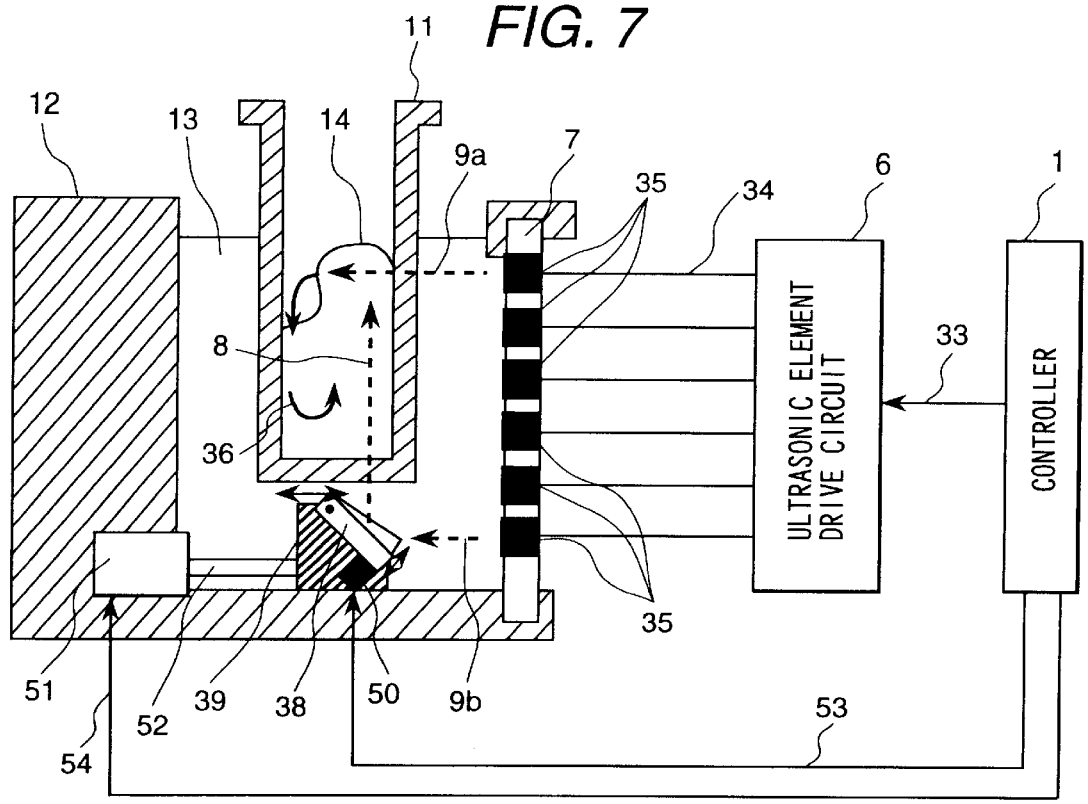
FIG. 7 is a schematic cross sectional view representing the major portion of the fourth embodiment according to the present invention.

FIG. 7 is a schematic cross sectional view representing the major part of the automatic analyzer according to the fourth Embodiment of the present invention. The portions other than the configuration shown in FIG. 7 are the same as those shown in the first Embodiment, so they will not be illustrated or described.

This fourth Embodiment shows an example of allowing change of the position of the ultrasonic reflecting mechanism 10 and the angle of the ultrasonic reflecting material 38 in the first and second Embodiments.

In FIG. 7, the reflecting material support mechanism 39 is connected with the drive mechanism 52, and drive mechanism 52 is connected with the reflecting mechanism traveling actuator 51 exemplified by the motor ands solenoid. Said reflecting mechanism traveling actuator 51 is actuated by the command from the controller 1 through reflecting mechanism traveling control signal 54, thereby changing the position in the heat insulating bath 12 of the reflecting material support mechanism 39.

The reflecting material 38 is connected to the reflecting material traveling actuator 50 exemplified by the piezoelectric element. Said reflecting material traveling actuator 50 is actuated upon receipt of a command from the controller 1 through the reflecting material angle control signal 53, and changes the angle of the reflecting material 38. Namely, the controller 1 changes the position of applying lower ultrasonic wave 8 and the angle of application in conformance to the amount of the specimen in the reaction vessel 11 and the material, size and shape of the reaction vessel 11. This makes it possible to correct the disposition for coordination between the lower ultrasonic wave and lateral ultrasonic wave on the specimen liquid level caused by the mechanical error of each system (deviation of the positions for application of the lower ultrasonic wave and lateral ultrasonic wave to generate swirling flow by agitation by coordination between lower ultrasonic wave and lateral ultrasonic wave).

The same effect as that of the first Embodiment cab be obtained according to the fourth Embodiment of the present invention.

The fourth Embodiment of the present invention makes it possible to change the position of applying lower ultrasonic wave 8 and the angle of application in conformance to the amount of specimen in the reaction vessel 11 and the material, size and shape of the reaction vessel 11. This makes it possible to correct the disposition for coordination between the lower ultrasonic wave and lateral ultrasonic wave on the specimen liquid level caused by the mechanical error of each system.

In the above-mentioned Embodiments of the present invention, ultrasonic wave generated from piezoelectric element 35 arranged toward the side wall in the reaction vessel 11 is reflected by the reflection board to generate lower ultrasonic wave. Instead of using a reflection board, it is also possible to lay out the piezoelectric element for generation of special-purpose lower ultrasonic wave at the position face to face with the bottom surface of reaction vessel 11, separately from the piezoelectric element to generate lateral ultrasonic wave. However, such configuration leads to complicated configuration as compared with the above-mentioned Embodiments according to the present invention.

Figure 8:
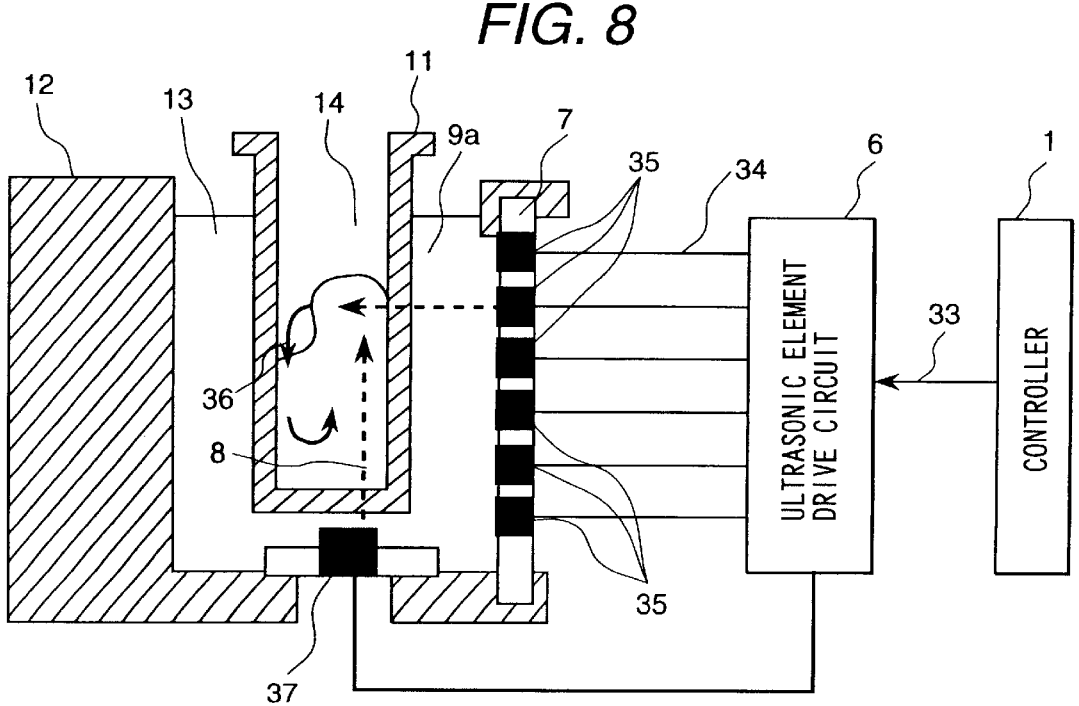
FIG. 8 is a schematic cross sectional view representing the comparative examples describing the effects of the present invention.
Figure 9A:
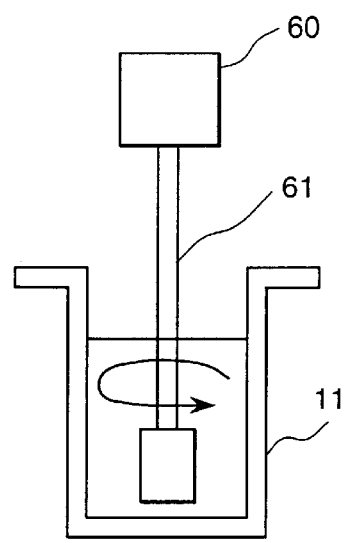
FIG. 9 is a drawing representing an example of the automatic analyzer in the prior art.
Figure 9B:
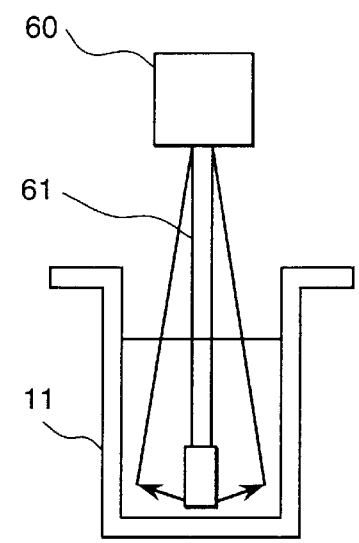
Figure 10A:
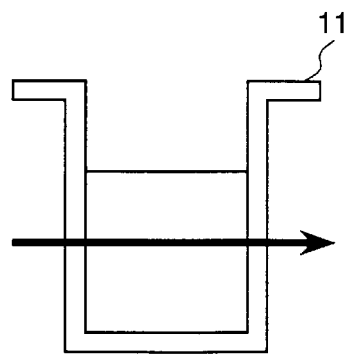
FIG. 10 is a drawing describing the problems raised by reduction in the amount of liquid and in the capacity of the reaction vessel.
Figure 10B:
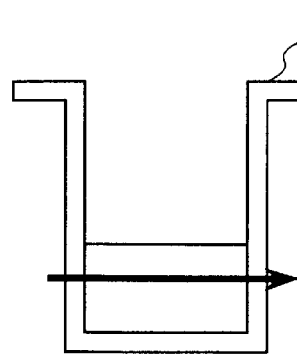
Figure 10C:
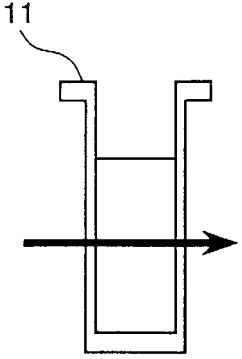

Namely, the piezoelectric element for lateral irradiation 35 to apply ultrasonic wave from the side of the reaction vessel 11 and the lower irradiation piezoelectric element 37 to apply ultrasonic wave from the bottom of the reaction vessel 11 are laid out, as shown in FIG. 8. Then the lower irradiation piezoelectric element 37 is actuated, and lower ultrasonic wave 8 is applied toward the liquid level of the specimen and reagent from the lower side of the reaction vessel 11 containing specimen and reagent. Part of the liquid level is raised by the acoustic radiation pressure of lower ultrasonic wave 8 to actuate piezoelectric element for lateral irradiation 35 and to generate lateral ultrasonic wave 9a, which is applied to the raised portion of the liquid level. Such configuration is also possible.

However, the configuration shown in FIG. 8 requires the agitation mechanism at one position to have both the piezoelectric element for lateral irradiation 35 and lower irradiation piezoelectric element 37. This will lead to complicated configuration and increased number of components.

Thus, the Embodiments of the present invention provide an automatic analyzer capable of ensuring an effective agitation of the reagent and specimen, hence, highly reliable results of analysis, despite the simple configuration and small size of the reaction vessel, without carry-over among specimens or water brought into the next process of analysis.

In the embodiment shown in FIG. 5, it is possible to lay out the means which change the angle of inclination of the bottom of heat insulating bath 12.

The present invention provides an automatic analyzer capable of ensuring an effective agitation of the reagent and specimen, hence, highly reliable results of analysis, despite the simple configuration and small size of the reaction vessel, without carryover among specimens or water brought into the next process of analysis.

(Fifth Embodiment)

Figure 11:
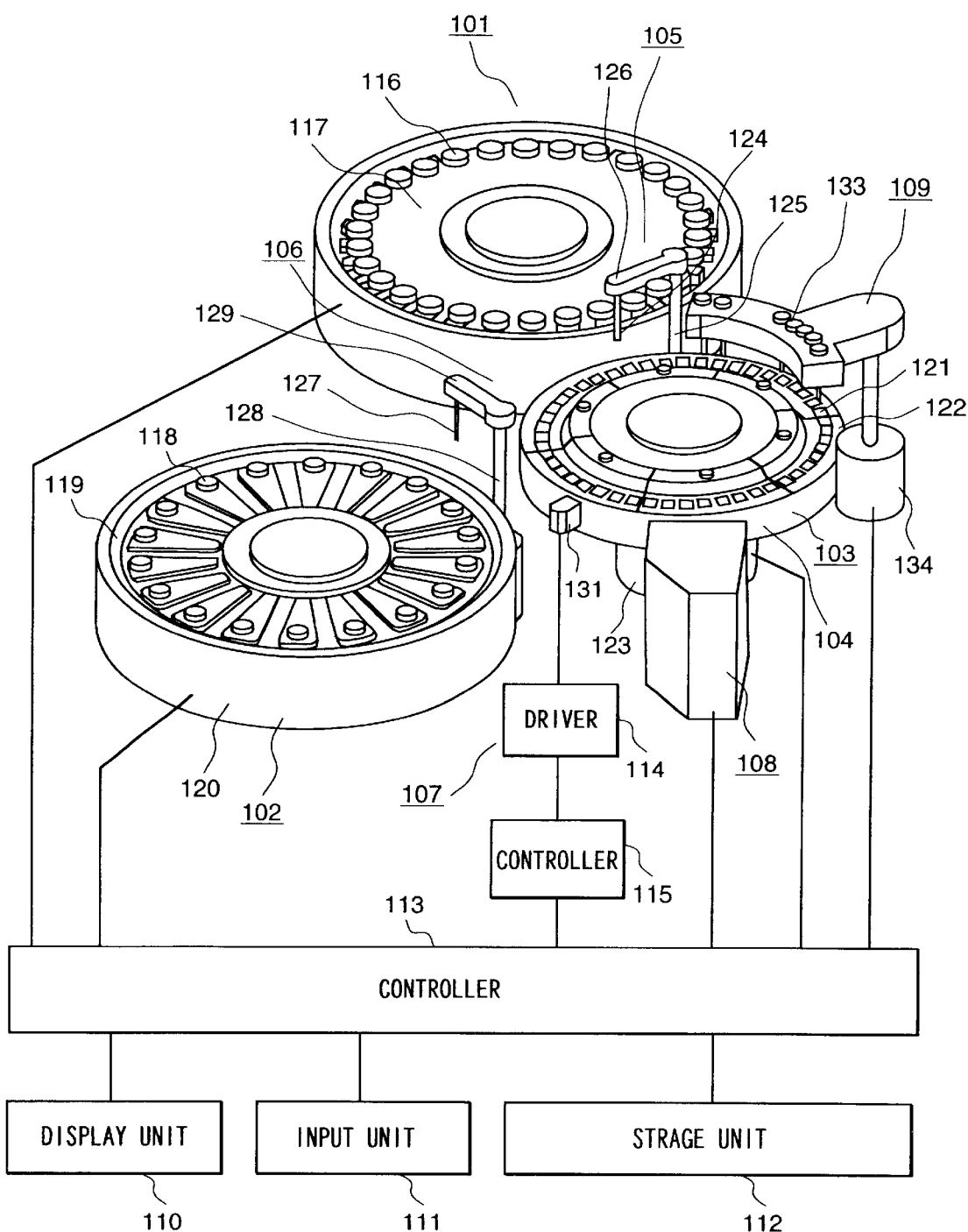
FIG. 11 is a perspective view representing the configuration of an automatic analyzer related to the embodiment according to the present invention.
Figure 12:
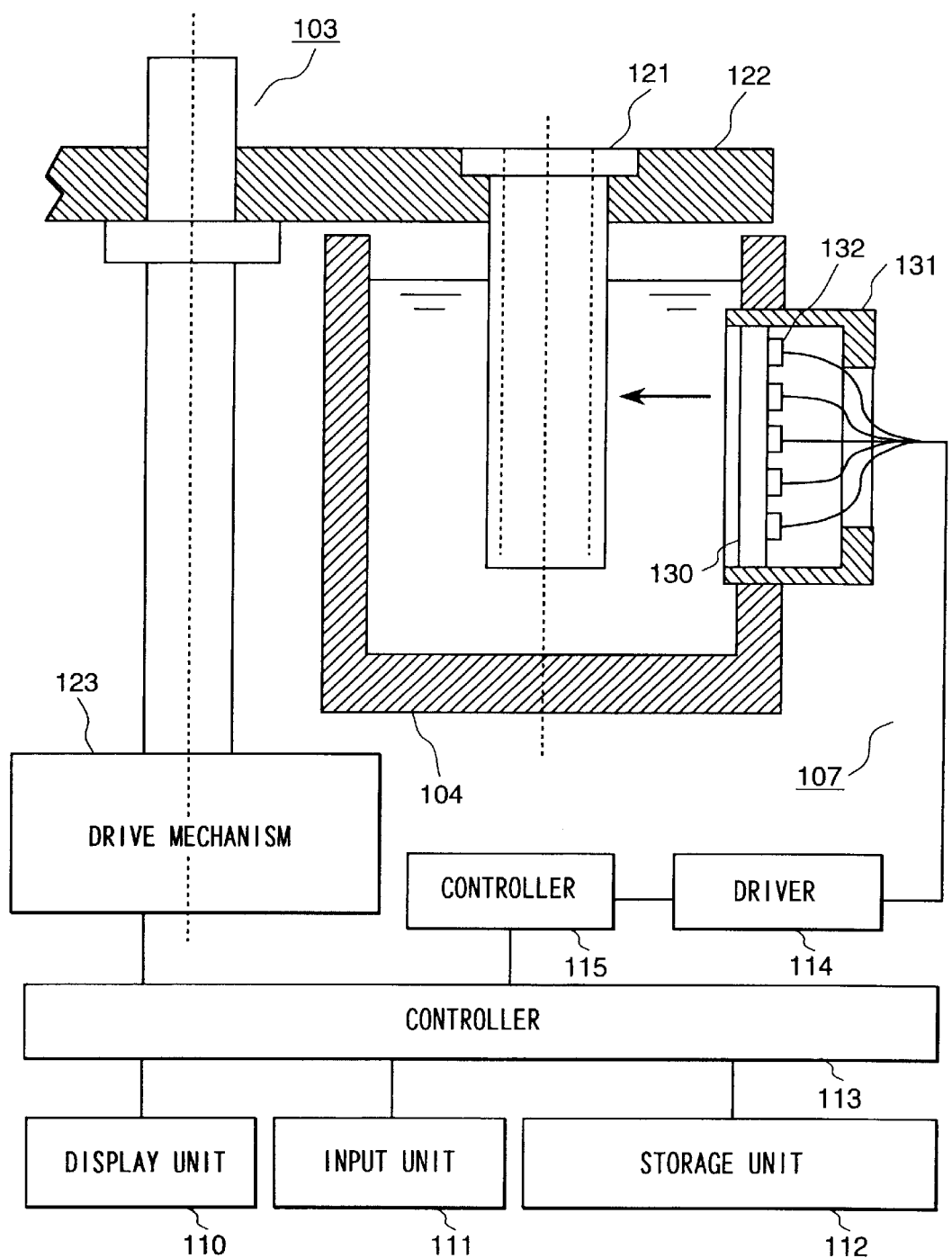
FIG. 12 is an vertical cross sectional view around the agitation mechanism of an automatic analyzer related to the embodiment according to the present invention.

FIG. 11 is a perspective view representing the configuration of an automatic analyzer related to the embodiments according to the present invention. FIG. 12 is a vertical cross sectional view around the agitating mechanism mounted on the automatic analyzer illustrated in FIG. 11.

As shown in FIG. 11, the automatic analyzer according to the present Embodiment mainly comprises a specimen disk 101, a reagent disk 102, a reaction disk 103, a reaction bath 104, a sampling mechanism 105, a pipetting mechanism 106, an agitating mechanism 107, a photometric mechanism 108, a cleaning mechanism 109, a display unit 110, an input unit 11, a storage unit 112 and a controller 113.

In FIG. 101, multiple specimen vessels 116 with sampled specimens mounted therein are arranged at fixed positions on the circumferences of circular disk 117 of the specimen disk 101, and the circular disk 117 is driven in the circumstantial direction by the drive mechanism comprising a motor and rotating shaft (not illustrated), etc. so that said disk can be positioned.

In FIG. 11, multiple reagent bottles 118 containing the reagent to cause reaction in a state mixed with the specimen are arranged at a fixed position on the circumference of the circular disk 119 of the reagent disk 102, and a temperature-controlled cold reserver 120 is provided around it. The circular disk 119 is driven in the circumstantial direction by the drive mechanism comprising a motor and rotating shaft (not illustrated), etc. so that said disk can be positioned.

In FIG. 11, multiple reaction vessel holders 122 holding the reaction vessel 121 to contain specimen and reagent are installed on the reaction disk 103, and a step of circumferential rotation and stop is repeated at a specified cycle by a drive mechanism 123, thereby allowing intermittent transfer of the reaction vessel 121.

In FIG. 11, the reaction bath 104 is installed along the travel path of the reaction vessel 121. It is a thermostatic bath to keep reaction solution in the reaction vessel 121 at a specified temperature in order to promote chemical reaction of the specimen and reagent by, for example, temperature controlled water. The reaction vessel 121 moves in the reaction bath 104.

In FIG. 11, sampling mechanism 105 comprises a probe 124, an arm 126 mounted on the bearing shaft 125, and a drive mechanism to permit reciprocating motion between the specimen disk 101 and reaction disk 103 using the bearing shaft 125 as a center of rotation. In conformance to the predetermined sequence, the specimen in the specimen vessel 116 fed to a specified position through the rotation of the specimen disk 101 is supplied to the reaction vessel 121. Similarly, the pipetting mechanism 106 comprises a probe 127, an arm 129 mounted on the bearing shaft 128, and a drive mechanism to permit reciprocating motion between the specimen disk 102 and reaction disk 103 using the bearing shaft 128 as a center of rotation. In conformance to the predetermined sequence, the reagent in the reagent bottle 118 fed to a specified position through the rotation of the specimen disk 102 is supplied to the reaction vessel 121. In this case, specimen vessel 116 and reagent bottle 118 contain specimens and reagents of different types, and a required quantity is fed to the reaction vessel 121.

In FIG. 11, an agitating mechanism 107 is a non-contact agitating mechanism to agitate and mix the specimen and reagent in the reaction vessel 121 by irradiation of acoustic wave from the side of the reaction vessel 121 fed to the position (position of agitation). It comprises stationary unit 131 fixed at the position where acoustic wave can be applied to the position of agitation from the side of the reaction vessel 121, a piezoelectric element driver 114 to drive the piezoelectric element (130 in FIG. 12), and agitating mechanism controller 115. Said agitating mechanism controller 115 is connected to controller 113 to drive piezoelectric element driver 114 and control the entire agitating mechanism 107.

In agitating mechanism 107, piezoelectric element 130 as a sound source is installed on the stationary unit 131 in such a way that its one side is immersed in the temperature controlled water of the reaction bath 104, as shown in FIG. 12. Said piezoelectric element 130 comprises multiple electrodes 132. Oscillation is given at a specified frequency by piezoelectric element driver 114, and the position for irradiation of acoustic wave can be changed by the electrode 132 to be oscillated.

In FIG. 12, reaction vessel 121 provided with the specimen and reagent is fixed to the reaction disk 103 by the reaction vessel holder 122. In conformance to rotation of the reaction disk 103 in the circumferential direction, it moves in a state immersed in the reaction bath 104 containing temperature controlled water. When it is shifted to the position of agitation and is stopped there, oscillation is given to piezoelectric element 130 at a specified frequency by piezoelectric element driver 114. Oscillation of the piezoelectric element 130 is transmitted as acoustic wave in the temperature controlled water of the reaction bath 104 to reach the side of the reaction vessel 121. Said acoustic wave passes through the wall surface of the reaction vessel 121, and reaches the specimen and reagent as internal agitated substances. Transmitted oscillatory wave acts on the gas/liquid boundary of the agitated substances to cause swirling flow. This swirling flow promotes movement of the specimen, allowing the specimen and reagent to be agitated, without the need of inserting the spatula, screw or the like into the reaction vessel 21.

To reinforce irradiation intensity, an acoustic lens can be installed in the direction of the oscillatory wave of the piezoelectric element 130. Said acoustic lens serves to condense oscillatory wave, and is effective especially when quick agitation is required.

Going back to FIG. 11, the photometric mechanism 108 comprises a light source, a photometer, a lens and a photometric signal processing unit (not illustrated). It measures the physical properties of the specimen by means of light; for example, it measure the absorbance of reaction solution in the reaction vessel 121. The cleaning mechanism 109 comprises multiple nozzles 133 and its vertical drive mechanism 134. Reaction solution in the reaction vessel 121 is sucked and the cleaning solution is discharged. Then the reaction vessel 121 fed to that position (cleaning position) is cleaned.

In FIG. 11, display unit 110 provides various screen displays including analysis items and results of analysis, and input unit 111 enters various types of information such as analysis items. Storage unit 112 stores the information on the predetermined sequence (program) to control each mechanism and analysis items.

The automatic analyzer according to the present Embodiment comprises a syringe, a pump, etc. in addition to the above-mentioned components. They are all controlled by the controller 113 according to the sequence stored in the storage unit 112.

The following describes the operation of the automatic analyzer configured as described above:

When the reaction vessel 121 cleaned by the cleaning mechanism 109 is driven by the reaction disk 103 and is fed to the specimen supply position, the specimen disk 101 rotates to feed the specimen vessel 116 containing the specimen to the sampling position. Similarly, the reagent disk 102 feeds the required reagent bottle 118 to the pipetting position.

This is followed by the operation of the sampling mechanism 105. The probe 124 is used to pour the specimen into the reaction vessel 121 fed to the specimen supply position from the specimen vessel 116 fed to the sampling position. The reaction vessel 121 containing the specimen is fed to the reagent supply position, and reagent is poured into the reaction vessel 121 fed to the reagent supply position from the reagent bottle 118 fed to the pipetting position on the reagent disk 102 by the operation of the pipetting mechanism 106.

After that, the reaction vessel 121 is fed to the position of agitation, and the specimen and reagent are agitated by means of the agitating mechanism 107.

The absorbance of the reaction solution having been agitated is measured by the photometric mechanism 108 when the reaction vessel 121 passes through the light source and photometer. This measurement is carried out several cycles. The reaction vessel 121 which has been measured is cleaned by the cleaning mechanism 109.

When such a series of operations is carried out for each reaction vessel 121, analysis by the automatic analyzer according to the present Embodiment is performed.

The following describes the characteristics of the embodiment with regard to agitation carried out by the agitating mechanism 107:

In the present Embodiment, the agitating mechanism 107 completes the following two preparatory steps in conformance to the command of the controller 113 by the time when the reaction vessel 121 is fed to the position of agitation:

(1) Determine acoustic wave irradiation position.

(2) Determine acoustic wave irradiation intensity.

The first step of preparation can be implemented, for example, by storing a table showing association between the analysis items and irradiation positions in the storage unit 112, and by searching the irradiation position corresponding to a particular analysis item, as shown in FIG. 13(*a*). Or it can also be implemented as follows: As shown in FIG. 13(*b*), a table showing association between the required amount of specimens and reagents for each analysis item is stored in the storage unit 112. The amounts of specimens and reagents corresponding to a particular analysis item are searched from this table. Then the liquid level in the reaction vessel 121 of the agitated substances (specimen and reagent) is calculated to determine the irradiation position based on the obtained liquid level.

The second step of preparation can be implemented, for example, by storing a table showing association between the analysis items and irradiation intensities in the storage unit 112, and by searching the irradiation intensity corresponding to a particular analysis item, as shown in FIG. 13(*c*). Especially, the irradiation intensity is preferred to be changed according to the reagent. Consequently, it can also be implemented by the following procedure: As shown in FIG. 13(*d*), the table showing the association between the information on each reagent and acoustic wave irradiation intensity is stored in storage unit 112, and irradiation intensity corresponding to a particular reagent is searched from this table.

For the irradiation position and irradiation intensity, it is also possible to take the following procedure: Multiple types of specified values are prepared as parameters in advance, and the optimum one of these parameters is selected with consideration given to kinetic characteristics of the agitated substance such as viscosity and surface tension. The selected value is described in the table. Especially, parameters of irradiation intensity are preferred to be parameters, not only frequency and voltage but irradiation time.

Those tables are stored in the storage unit 112 by manual reading of the operator or automatic reading.

The above two steps of preparation allows the agitating mechanism 107 to provide effective agitation in conformance to analysis item.

Namely, when the reaction vessel 121 is fed to the point of agitation and is stopped there, agitating mechanism controller 115 controls the piezoelectric element 130 to ensure that acoustic wave irradiated from the electrode 132 which irradiates acoustic wave to the irradiation position determined in the first preparatory step in conformance to the command of the controller 113 through piezoelectric element driver 114 will have the irradiation intensity determined in the second step of preparation. As described above, acoustic wave is applied to the gas/liquid boundary level of the object to be agitated having the level different in conformance to the analysis item. Acoustic wave irradiation intensity is selected with consideration given to kinetic characteristics such as viscosity and surface tension of the agitated substances, thereby ensuring effective agitation to be performed.

In the above-mentioned embodiment, irradiation intensity is determined using the table stored in the storage unit 112. In another embodiment, it is possible to use information recorded in the reagent bottle 118.

For example, the barcode showing irradiation intensity of acoustic wave is pasted on each reagent bottle 118. A barcode reader to read it can be installed close to the reagent disk 102. Similarly to the above-mentioned case, for irradiation intensity, multiple types of specified values are prepared as parameters in advance, and the optimum one of these parameters can be selected with consideration given to kinetic characteristics of the agitated substance such as viscosity and surface tension. Then the barcode showing irradiation intensity can be pasted. Also similarly to the above case, parameters of irradiation intensity are preferred to be a combination of parameters, not only frequency and voltage but irradiation time.

This allows the same barcode to be pasted on the reagent having the same irradiation intensity. It also allows the reagents bearing the same barcode to be handled collectively. This will result in reduced amount of information; hence, reduced loads of storage unit 112 and controller 113.

In still other embodiment, it is possible to use the information entered by the operator through the input unit 11, without using the information assigned to the reagent bottle 118.

Similarly to the above, for irradiation intensity in this case, multiple types of specified values are prepared as parameters in advance, and the optimum one of these parameters can be selected by the operator with consideration given to kinetic characteristics of the agitated substance such as viscosity and surface tension. Also similarly to the above case, parameters of irradiation intensity are preferred to be a combination of parameters, not only frequency and voltage but irradiation time. A combination of these parameters can be selected as one parameter by the operator. This does not required the complicated work to be done by the operator.

In the above-mentioned embodiments, agitation is conducted at only one position. Agitation can be made at two or more places, depending on the system size. For example, piezoelectric element 130 can be installed on the bottom of the reaction bath 104 to allow simultaneous irradiation of acoustic wave to the side and bottom surface of the reaction vessel 121 from both the side and bottom.

For example, assume an analysis item which requires use of two or more types of reagents, and two or more reagent inlet positions. To ensure that agitation is carried out every time reagent is poured through each reagent inlet position, two or more positions for agitation can be provided.

As described above, when the specimen and reagent poured into a reaction vessel are to be analyzed, the present invention allows agitation to be carried out by irradiation of acoustic wave, without contacting the specimen and reagent in the reaction vessel. At the same time, it ensures an effective agitation for each object to be analyzed.

What is claimed is:

1. An automatic analyzer comprising;

an analyzer unit to analyze components of a specimen to be analyzed, a heat insulating bath to support a reaction vessel and to hold a heat insulating medium to keep a constant temperature of liquid mixture of said specimen for analysis stored in said reaction vessel and reagent or others, a controller to administer and control the automatic analyzer including said analyzer unit, a lateral ultrasonic generator installed on a side of the reaction vessel supported by said heat insulating bath to generate lateral ultrasonic wave, a lower ultrasonic generator to irradiate a lower ultrasonic wave toward the liquid level of liquid mixture from the bottom of said reaction vessel, and an ultrasonic generator drive circuit to supply drive power to said lateral ultrasonic generator and said lower ultrasonic generator.

2. An automatic analyzer as defined in claim 1, wherein at least one of position and angle of said lower ultrasonic generator is installed so that a liquid level of the liquid mixture being closer to the lateral ultrasonic generator than a center of the liquid mixture is raised higher.

3. An automatic analyzer comprising;

an analyzer unit to analyze components of a specimen to be analyzed, a heat insulating bath to support a reaction vessel and to hold a heat insulating medium to keep a constant temperature of liquid mixture of said specimen for analysis stored in said reaction vessel and reagent or others, wherein the bottom of said insulating bath is inclined with respect to said liquid mixture level to serve as an ultrasonic wave reflecting means, a controller to administer and control the automatic analyzer including said analyzer unit, an agitator installed on a side of the reaction vessel supported by said heat insulating bath, wherein
said agitator comprises multiple ultrasonic generators to generate lateral ultrasonic wave, and
said agitator mixes and agitates the specimen in the reaction vessel, reagent or the like;

wherein a position and angle of the bottom is provided so that a liquid level of the liquid mixture being closer to the lateral ultrasonic generator than a center of the liquid mixture is raised higher by a function of a lower ultrasonic wave reflected from the bottom of said reaction vessel toward the liquid mixture level and said lateral ultrasonic wave, and an ultrasonic generator drive circuit to supply drive power to said ultrasonic generator.

4. An automatic analyzer comprising;

an analyzer unit to analyze components of a specimen to be analyzed, a reaction vessel storing the specimen for analysis and liquid mixture with reagent or the like, wherein a bottom of said reaction vessel is inclined with respect to said liquid mixture level to serve as an ultrasonic wave reflecting means, a heat insulating bath to support said reaction vessel and to hold a heat insulating medium to keep a constant temperature of liquid mixture of said specimen for analysis stored in said reaction vessel and reagent or others, a controller to administer and control the automatic analyzer including said analyzer unit, an agitator installed on the side of a reaction vessel supported by said heat insulating bath, wherein
said agitator comprises multiple ultrasonic generators to generate lateral ultrasonic wave, and
said agitator mixes and agitates the specimen in the reaction vessel, reagent or the like;

wherein a position and angle of the bottom is provided so that a liquid level of the liquid mixture being closer to the lateral ultrasonic generator than a center of the liquid mixture is raised higher by a function of a lower ultrasonic wave reflected from the bottom of said reaction vessel toward the liquid mixture level and said lateral ultrasonic wave, and an ultrasonic generator drive circuit to supply drive power to said ultrasonic generator.

5. An automatic analyzer according to claim 1, characterized in that said ultrasonic wave reflecting means comprises material having acoustic impedance different from that of the heat insulating medium in the heat insulating bath which transmits ultrasonic wave generated from the ultrasonic generator.

6. An automatic analyzer according to claim 1, characterized in that said ultrasonic wave reflecting means comprises a mechanism to change the ultrasonic irradiation position and ultrasonic irradiation angle.

* * * * *